United States Patent [19]

Cassidy et al.

[11] Patent Number: 4,987,138

[45] Date of Patent: Jan. 22, 1991

[54] ACTIVE COMPOUNDS

[75] Inventors: Frederick Cassidy; Geoffrey Stemp, both of Harlow, England

[73] Assignee: Beecham Group p.l.c., England

[21] Appl. No.: 231,183

[22] Filed: Aug. 11, 1988

Related U.S. Application Data

[63] Continuation of Ser. No. 905,695, Sep. 9, 1986, abandoned.

[30] Foreign Application Priority Data

Sep. 11, 1985 [GB] United Kingdom ............... 8522492
Sep. 18, 1985 [GB] United Kingdom ............... 8523051

[51] Int. Cl.$^5$ .................. A61K 31/35; A61K 31/40;
A61K 31/445; C07D 311/58
[52] U.S. Cl. .................................. 514/320; 514/278;
514/409; 514/422; 514/456; 546/15; 546/196;
548/407; 548/525; 549/345; 549/399
[58] Field of Search .............. 549/399, 345; 514/456,
514/278, 320, 422, 409; 546/196, 15; 548/407,
525

[56] References Cited

U.S. PATENT DOCUMENTS

| | | | |
|---|---|---|---|
| 4,062,870 | 12/1977 | Watts | 549/399 X |
| 4,446,113 | 5/1984 | Evans et al. | 549/399 X |
| 4,481,214 | 11/1984 | Evans | 549/399 X |
| 4,555,509 | 11/1985 | Evans et al. | 549/399 X |
| 4,575,511 | 3/1986 | Evans et al. | 549/399 X |
| 4,629,734 | 12/1986 | Ashwood | 549/399 X |
| 4,644,070 | 2/1987 | Evans et al. | 549/399 |

FOREIGN PATENT DOCUMENTS 0076075 4/1983 European Pat. Off. .

OTHER PUBLICATIONS

Bhattacharya, et al., C.A.:103:123289d (1985).

Primary Examiner—Joseph Paul Brust
Attorney, Agent, or Firm—Jacobs & Jacobs

[57] ABSTRACT

Compounds of formula (I) and pharmaceutically acceptable salts thereof:

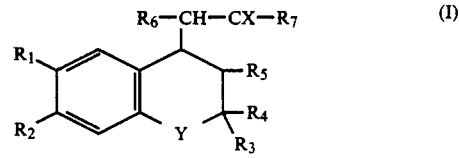

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethenyl terminally substituted by $C_{1-6}$ alkylcarbonyl, nitro or cyano, or —C($C_{1-6}$ alkyl)(NOH) or —C($C_{1-6}$ alkyl)NNH$_2$ or, when Y is oxygen, one of $R_1$ and $R_2$ is nitro, cyano or $C_{1-3}$ alkylcarbonyl and the other is methoxy or amino optionally substituted by $C_{2-7}$ alkanoyl;
one of $R_3$ and $R_4$ is hydrogen or $C_{1-4}$ alkyl and the other is $C_{1-4}$ alkyl or $R_2$ and $R_3$ together are $C_{2-5}$ polymethylene;
$R_5$ is hydroxy, $C_{1-6}$ alkoxy or $C_{1-7}$ acyloxy;
$R_6$ is hydrogen or $C_{1-6}$ alkyl;
$R_7$ is NR$_8$R$_9$ wherein R$_8$ and R$_9$ are independently $C_{1-6}$ alkyl, R$_8$ is hydrogen and R$_9$ is $C_{1-6}$ alkyl or R$_8$ and R$_9$ together are $C_{4-5}$ polymethylene; or R$_6$ and R$_8$ together are —(CH$_2$)$_n$— wherein n is 2 or 3, and R$_9$ is hydrogen or $C_{1-6}$ alkyl; or R$_7$ is CH$_2$R$_{10}$ wherein R$_{10}$ is hydrogen or $C_{1-5}$ alkyl optionally substituted by halo, hydroxy or $C_{1-6}$ alkoxy; or R$_6$ and R$_{10}$ are —(CH$_2$)$_m$— wherein m is 2 or 3;
X is oxygen or sulphur; and
Y is oxygen, CH$_2$ or NH;
the R$_6$—CH—CX—R$_7$ group being trans to the R$_5$ group; having blood pressure lowering activity, a process for their preparation and their use as pharmaceuticals.

16 Claims, No Drawings

ACTIVE COMPOUNDS

This is a continuation application of Ser. No. 905,695, filed Sept. 9, 1986, now abandoned.

The present invention relates to novel compounds having pharmacological activity, to a process for preparing them, to pharmaceutical compositions containing them, and to their use.

A class of compounds have been found to have blood pressure lowering activity, useful in the treatment of hypertension. In addition, these compounds are believed to be $K^+$ channel activators which indicates that they are of potential use in the treatment of disorders associated with smooth muscle contraction of the gastro-intestinal tract, respiratory system, uterus or urinary tract. Such disorders include peptic ulcers, irritable bowel syndrome and diverticular disease, reversible airways obstruction and asthma; premature labour; and incontinence. They are also indicated as of potential use in the treatment of cardiovascular disorders other than hypertension, such as congestive heart failure, angina, peripheral vascular disease and cerebral vascular disease.

Accordingly, the present invention provides a compound of formula (I) or a pharmaceutically acceptable salt thereof:

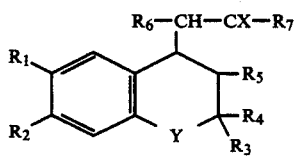

(I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulpnonyl, $C_{1-6}$ alkylcarbonylanino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl or aminosulphinyl, aminosulpnonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethenyl terminally substituted by $C_{1-6}$ alkylcarbonyl, nitro or cyano, or -C($C_{1-6}$ alkyl(NOH) or —C($C_{1-6}$ alkyl)NNH$_2$ or, when Y is oxygen, one of $R_1$ and $R_2$ is nitro, cyano or $C_{1-3}$ alkylcarbonyl and the other is methoxy or amino optionally substituted by $C_{2-7}$ alkanoyl;

one of $R_3$ and $R_4$ is hydrogen or $C_{1-4}$ alkyl and the other is $C_{1-4}$ alkyl or $R_2$ and $R_3$ together are $C_{2-5}$ polymethylene;

$R_5$ is hydroxy, $C_{1-6}$ alkoxy or $C_{1-7}$ acyloxy;

$R_6$ is hydrogen or $C_{1-6}$ alkyl;

$R_7$ is NR$_8$R$_9$ wherein $R_8$ and $R_9$ are independently $C_{1-6}$ alkyl, $R_8$ is hydrogen and $R_9$ is $C_{1-6}$ alkyl or $R_8$ and $R_9$ together are $C_{4-5}$ polymethylene; or $R_6$ and $R_8$ together are —(CH$_2$)$_n$— wherein n is 2 or 3, and $R_9$ is nydrogen or $C_{1-6}$ alkyl; or $R_7$ is CH$_2$R$_{10}$ wherein $R_{10}$ is hydrogen or $C_{1-5}$ alkyl; or $R_6$ and $R_{10}$ are —(CH$_2$)$_m$— wherein m is 2 or 3;

X is oxygen or sulphur; and
Y is oxygen, CH$_2$ or NH;
the $R_6$—CH—CX—R$_7$ group being trans to the $R_5$ group.

When one of $R_1$ and $R_2$ is hydrogen, the other is, preferably, selected from the class of halo, CF$_3$, $C_{1-6}$ alkylcarbonyl, $C_{1-6}$ alkoxycarbonyl, nitro or cyano. In particular, when one of $R_1$ and $R_2$ is hydrogen, the other is, preferably, acetyl, chloro, CF$_3$, nitro or cyano, especially CF$_3$, nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is, preferably, amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is CF$_3$, nitro, cyano or $C_{1-3}$ alkylcarbonyl, it is preferred tnat $R_1$ is CF$_3$, nitro, cyano or $C_{1-3}$ alkylcarbonyl.

The alkyl groups or alkyl moieties of alkyl-containing groups for $R_1$ or $R_2$ are, preferably methyl or ethyl.

Preferably, $R_3$ and $R_4$ are both $C_{1-4}$ alkyl, in particular both methyl.

Preferred examples of $R_5$ include methoxy and ethoxy, of which methoxy is more preferred. When $R_5$ is $C_{1-7}$ acyloxy a preferred class of $R_5$ is unsubstituted carboxylic acyloxy, such as unsubstituted aliphatic acyloxy or benzoyloxy. However, it is preferred that $R_5$ is hydroxy.

Examples of $R_6$ include hydrogen, methyl, ethyl, n- or iso-propyl. Preferably, $R_6$ is hydrogen or methyl, especially hydrogen, or with $R_7$ as defined below.

When $R_7$ is NR$_8$R$_9$ examples of $R_8$ and $R_9$, include hydrogen (for $R_8$), methyl, ethyl, n- and iso-propyl, and n-, iso-, sec- and t-butyl, $C_4$ or $C_5$ polymethylene or $R_8$ together with $R_6$ is —(CH$_2$)$_2$— or —(CH$_2$)$_3$—, and $R_9$ is hydrogen or an alkyl group as described above. Preferably $R_8$ and $R_9$ are each methyl or R$_6$CHCXNR$_8$R$_9$ forms a pyrrolidone or piperidone ring and $R_9$ is methyl.

Examples of $R_{10}$, when $C_{1-5}$ alkyl, include methyl, ethyl and n- and iso-propyl or $R_{10}$ together with $R_6$ is —(CH$_2$)$_2$— or —(CH$_2$)3—. Preferably $R_{10}$, when $C_{1-6}$ alkyl, is methyl.

X preferably represents oxygen.
Y preferably represents oxygen.
Examples of a pharmaceutically acceptable salt of a compound of formula (I) include the acid addition salts of a compound of formula (I), wherein one or other of $R_1$ and $R_2$ is amino or an amino-containing group, for example the hydrochloride and hydrobromide salts.

Examples of a pnarmaceutically acceptable solvate of a compound of formula (I) include the hydrate.

Preferably, a compound of formula (I) is in substantially pure form or in crystalline form.

The compounds of formula (I) are asymmetric and, therefore, can exist in the form of optical isomers. The present invention extends to all such isomers individually and as mixtures, such as racemic modifications.

Compounds of the formula (I) and their pharmaceutically acceptable salts may form pharmaceutically acceptable solvates, and the invention extends to such solvates.

A preferred group of compounds within formula (I) is of formula (II):

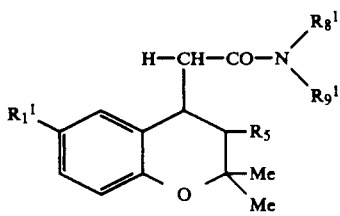

wherein:
$R_1^1$ is nitro, cyano, $CF_3$ or $C_{1-6}$ alkylcarbonyl;
$R_8^1$ and $R_9^1$ are independently $C_{1-6}$ alkyl; and $R_5$ is as defined in formula (I),
the compound being in the trans-configuration as defined in formula (I).

In formula (II):
$R_1^1$ is preferably cyano;
$R_5$ is preferably hydroxy.

Preferred values for the remaining variables are as described under formula (I).

Another group of compounds within formula (I) is of formula (III):

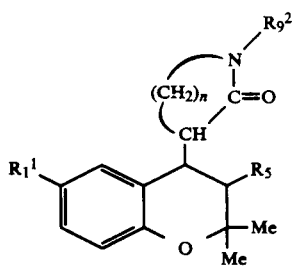

wherein
$R_9^2$ is $C_{1-6}$ alkyl and the remaining variables are as hereinbefore defined.

Preferred values for the variables are as described for the corresponding variables under formulae (I) and (II).

A further group of compounds within formula (I) is of formula (IV):

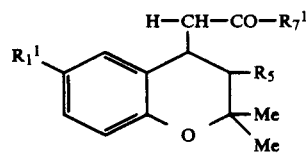

wherein:
$R_7^1$ is $C_{1-6}$ alkyl and the remaining variables are as hereinbefore defined.

The present invention also provides a process for the preparation of a compound of formula (I) or a pharmaceutically acceptable salt thereof, which process comprises reacting a compound of formula (V):

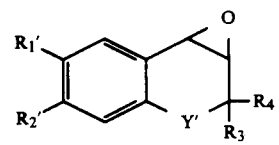

wherein
$R_1'$ and $R_2'$ are $R_1$ and $R_2$ as hereinbefore defined or a group or atom convertible thereto;
$Y'$ is Y as hereinbefore defined or a moiety convertible thereto; and
$R_3$ and $R_4$ are as hereinbefore defined;
with the anion of a compound of formula (VI):

$$R_6CH_2COR_{11} \qquad (VI)$$

wherein $R_{11}$ is $NR_8' R_9$ or $CHR_{10}CO_2R_{12}$ wherein $R_{12}$ is $C_{1-6}$ alkyl or benzyl, $R_8'$ is $R_8$ or an amino protecting group and $R_6$, $R_9$ and $R_{10}$ are as hereinbefore defined; to give a compound of formula (VII):

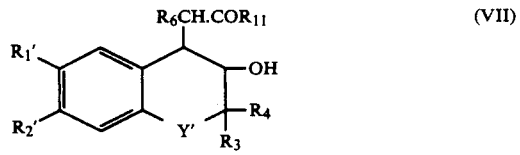

wherein the variables are as hereinbefore defined; and thereafter in the compound of formula (VII); if necessary, converting $R_{11}$ to $R_7$; when $R_1'$ or $R_2'$ is a group or atom convertible to $R_1$ or $R_2$ as hereinbefore defined, converting $R_1'$ to $R_1$ and/or $R_2'$ to $R_2$; converting $R_8'$ to $R_8$; when $Y'$ is a moiety convertible to Y, converting $Y'$ to Y; optionally converting $R_5$ hydroxy to other $R_5$ as hereinbefore defined; and optionally thiating the carbonyl group depicted in formula (VII).

The anion of the compound of formula (VI) may be generated by any conventional method, for example with a base such as lithium diisopropylamide. The reaction between the compounds of formulae (V) and (VI) is preferably carried out in a solvent such as tetrahydrofuran at a temperature of −70° to reflux, depending on the nature of the anion (VI).

A method for the synthesis of the compound of formula (VII) wherein $R_{11}$ is $CHR_{10}CO_2R_{12}$ which may be used is that of G. R. Kieczykowski, M. L. Quesada and R. H. Schlessinger. J. Amer. Chem. Soc., 782, 102, 1980 as exemplified in the Description hereinafter.

A compound of formula (VII) wherein $R_{11}$ is $CHR_{10}CO_2R_{12}$ may be converted to a compound of formula (I) wherein $R_7$ is $CH_2R_{10}$, by deesterification followed by decarboxylation.

Deesterification may be effected conventionally, the most appropriate method depending to some extent on the nature of the group $R_{12}$. However, basic reaction conditions will generally be applicable. The process conditions described hereinafter for the decarboxylation in the presence of base are in general suitable for this deesterification.

When $R_{12}$ is, for example, a tert-butyl group, deesterification may also be effected conventionally in the presence of acid such as trifluoroacetic acid or aqueous hydrochloric acid. Reaction may be effected at ambient temperature or a slightly higher temperature.

When $R_{12}$ is for example a benzyl group, deesterification may also oe effected conventionally by hydrogenolysis, for example by transition-metal catalysed hydrogenation, such as that using palladium/charcoal.

The decarboxylation is conveniently effected by treatment with a moderately strong base optionally in an aqueous reaction medium.

Examples of bases for the reaction include inorganic bases such as sodium hydroxide. Examples of reaction media include water, usually in admixture with a water-miscible solvent such that the compound is soluble therein. Examples include aqueous alcohols such as aqueous ethanol and aqueous polyethers such as aqueous dioxan. Reaction is conveniently effected at a moderately elevated temperature, such as 50° to 150° C., conveniently at the boiling point of the reaction medium.

Alternatively the decarboxylation may be effected by heating to a non-extreme temperature, for example 60° to 150° C. in an inert solvent, such as benzene, toluene or xylene, for example at solvent boiling point.

Spontaneous decarooxylation may occur under the reaction conditions for tne deesterification of the compound of formula (VII). Even where this is not the case, it is convenient to decarboxylate the $CHR_{10}CO_2H$ compound in situ without isolation. It is especially convenient to carry out the conversion $CHR_{10}CO_2R_{12}$ to $CH_2R_{10}$ as a single-step one-pot process, by treatment with a moderately strong base optionally in an aqueous reaction medium. Suitable conditions are as hereinbefore described for decarboxylation.

If a compound of formula (I) is desired wherein $R_1/R_2$ contains a ketonic CO group, e.g. $C_{1-6}$ alkylcarbonyl, and X is S, it will generally be desirable to protect the CO group in $R_1/R_2$ during thiation of the group X when it is O.

This may be effected in an intermediate in the synthesis of the compound of formula (V), giving rise to a $R_1'$ or $R_2'$ as defined. Examples of protected groups in this case include ketalised carbonyl groups, which may be protected and deprotected conventionally. Alternatively, protection of this type may be effected in the compound of formula (VII) prior to thiation.

Examples of an optional conversion of $R_1/R_2$ in the resulting compound of formula (I) into another $R_1/R_2$, as hereinbefore defined, include the optional conversion of an α-hydroxethyl group into acetyl by oxidation, the optional conversion of a hydrogen atom into a nitro group by nitration, or the optional conversion of halogen to cyano by nucleophilic displacement with, for example, CuCN.

When $R_8$ in formula (I) is hydrogen, it is preferred that $R_8'$ in formula (VI) is an amino protecting group, such as benzyl optionally substituted by one or more $C_{1-6}$ alkoxy groups. A preferred protecting group is p-methoxybenzyl, removable by acidic hydrolysis using methanesulphonic acid.

It will be appreciated that compounds of the formula (I), but wherein $R_8$ is replaced by $R_8'$, when an amino protecting group are useful, novel intermediates, and form an aspect of the invention.

When Y in formula (I) is NH, the group Y' convertible thereto may be $NR_{13}$ where $R_{13}$ is an N-protecting group such as an acyl group, for example $C_{2-5}$ alkanoyl e.g. acetyl and propionyl; benzoyl, phthaloyl or readily hydrogenolysable groups such as benzyl or benzyloxycarbonyl.

Preferably an $R_{13}$ protecting group is $C_{2-5}$ alkanoyl such as acetyl or propionyl. Such groups may be removed by conventional hydrolysis.

An $R_{13}$ acetyl group is particularly easily removed and may therefore under certain conditions be converted to hydrogen by chromatograpnic methods, such as on a silica gel column.

Examples of an optional conversion of $R_5$ hydroxy in a compound of formula (VII) into another $R_5$ are generally known in the art. For example, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of a condensation promoting agent, such as a base.

The optional thiation of the carbonyl group depicted in formula (VII) may be carried out with conventional thiation agents, such as hydrogen sulphide, phosphorus pentasulphide or Lawesson's reagent (p-methoxyphenenylthiophosphine sulphide dimer). The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably. acid catalysed by, for example, hydrogen chloride in a polar solvent, such as acetic acid or ethanol. The preferred use of Lawesson's reagent is preferably carried out under reflux in a dry solvent, sucn as toluene or methylene chloride.

It is preferred that a compound of formula (I), or a pharmaceutically acceptable solvate thereof is isolated from the preparative process hereinbefore in substantially pure or crystalline form.

The compounds of formula (V) in which Y' is oxygen are known compounds or may be prepared by processes analogous to those for preparing known compounds. The method of preparation of these compounds is disclosed in U.S. Pat. No. 4,110,347, the disclosure of which is incorporated herein by way of reference.

A compound of formula (V) in which Y' is $NR_{13}$ may be prepared by reacting a compound of formula (VIII):

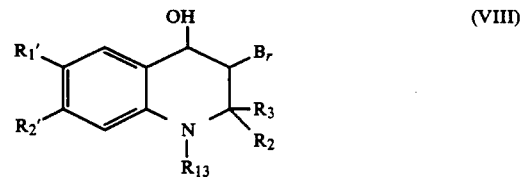

(VIII)

wherein $R_{13}$ is as defined, preferably acetyl and the remaining variables are as hereinbefore defined; with a base, such as potassium hydroxide, in ether or aqueous dioxan.

Compounds of the formula (VIII) may be prepared in accordance with known processes, for example as described in the following Scheme:

Scheme

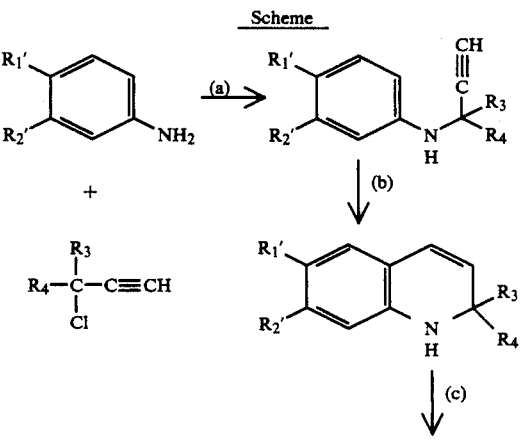

-continued
Scheme

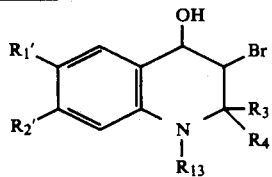
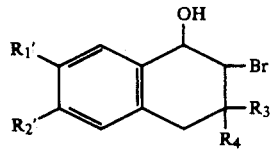

(a) Room temperature; triethylamine; copper (I)chloride, copper bronze; water; ether.

(b) Heat to 80° C.; copper (I) chloride in dioxan under $N_2$.

(c) Optional N-protection e.g. acetylation with acetyl chloride in N,N-dimethylaniline in dichloromethane; then N-bromo succinimide/dimethylsulphoxide/water.

The above process can produce mixtures of compounds during reaction (b) owing to the two sites available for ring formation. It is therefore advisable to remove any of the undesired compound by, for example, chromatography, before reaction (c).

Instead of carrying out the conversion of $R_1'$ or $R_2'$ when a group or atom convertiole into $R_1$ or $R_2$ after reacting a compound of formula (V) with an anion of formula (VI), it is greatly preferred that any such conversions are carried out at an earlier stage, preferably on the dihydroquinoline produced after reaction (b) above. In other words, it is preferred that, for the process of the invention when Y' is $NR_{13}$ or NH, $R_1'$ is $R_1$ and $R_2'$ is $R_2$, except when $R_1$ is cyano, in which case the conversion or interconversion to $R_1$ cyano is preferably carried out after the reaction of the compounds of formulae (V) and (VI).

Methods for the preparation of compounds of formula (V) wherein Y' is $NR_{13}$ are also described in PCT/GB84/00252.

A compound of formula (V) in which Y' is $CH_2$, may be prepared by reacting a compound of formula (IX):

wherein the variable groups are as hereinbefore defined, the bromo atom being trans to the hydroxy group, with a base, such as potassium hydroxide, in a solvent, such as ether or aqueous dioxan.

A compound of formula (IX) may be prepared by reacting a compound of formula (X):

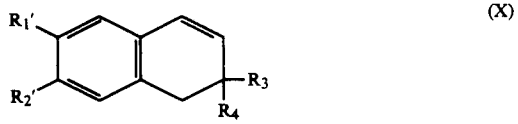

wherein the variables are as hereinbefore defined, with N-bromosuccinimide in a solvent, such as aqueous dimethyl sulphoxide.

A compound of formula (X) may be prepared in accordance with any appropriate known process. For example, a compound of formula (X) may be prepared by the process depicted below:

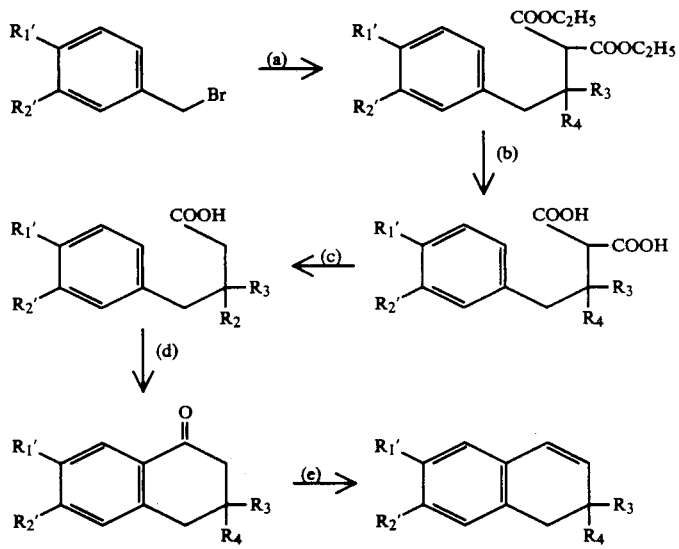

Reaction (a)

A Grignard reagent is formed from the benzyl bromide by reaction with magnesium in dry ether under reflux. The complex is then treated with copper (I) chloride and the product is then reacted witn a compound of formula:

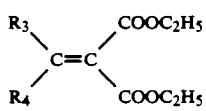

wherein $R_3$ and $R_4$ are as hereinbefore defined.

Reaction (b)

The diester is deesterified conventionally using potassium hydroxide in aqueous ethanol.

Reaction (c)

The diacid is mono-decarboxylated at an elevated temperature.

Reaction (d)

The acid is dehydrated with concomitant cyclisation using polyphosphoric acid at elevated temperatures.

Reaction (e)

The naphthalenone in dry ethanol is reduced with sodium borohydride to give the corresponding alcohol which is then treated under reflux with para-toluenesulphonic acid in benzene.

Methods for the preparation of compounds of formula (V) wherein Y' is $CH_2$ are also described in EP-A-168619.

As mentioned previously, the compounds of formula (I) have been found to have blood-pressure lowering activity. They are therefore useful in the treatment of hypertension. They may also be of potential use in the treatment of other disorders hereinbefore described.

The present invention accordingly provides a pharmaceutical composition which comprises a compound of this invention, in particular a compound of formula (I), or a pharmaceutically acceptable salt thereof, together with a pharmaceutically acceptable carrier.

The compositions are preferably adapted for oral administration. However, they may be adapted for other modes of administration, for example parenteral administration for patients suffering from heart failure.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension in mammals including humans, which comprises administering to the sufferer an anti-hypertensively effective amount of a compound of formula (I) or a pharmaceutically acceptable solvate thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

At the above mentioned dosage ranges, no toxiological effects are indicated for the compounds of the invention.

The present invention provides a compound of the invention, in particular a compound of formula (I) or a pharmaceutically acceptable solvate thereof for pharmaceutical use, in particular for use in the treatment of hypertension.

The following Examples illustrate the preparation of compounds of formula (I); the following descriptions illustrate the preparation of intermediates

Description 1

6-Cyano-3,4-dihydro-3-hydroxy-N-methyl-N-(4-methoxybenzyl)-2,2-dimethyl-2H-1-benzopyran-4-acetamide

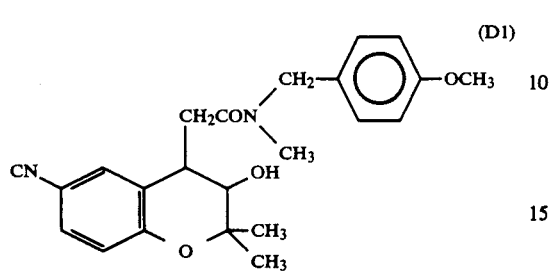
(D1)

n-Butyllithium (6.7 ml of 1.5 M solution in hexane, 10 mmol) was added droPwise to a solution of diisopropylamine (1.4 ml, 10 mmol) in dry tetranydrofuran (10 ml) at 0° C., under nitrogen. A solution of N-methyl-N-(4-metnoxybenzyl)-acetamide (1.93 g, 10 mmol) in tetrahydrofuran (10 ml) was then added and the solution stirred for 0.5 h. A solution of 6-cyano-3,4-epoxy-3,4-dihyro-2,2-dimethyl-2H-1-benzopyran (2.0 g, 10 mmol) in tetrahydrofuran (20 ml) was then added, and the mixture allowed to warm to room temperature, and then heated under reflux for 2 hours. After cooling, the mixture was partitioned between etnyl acetate and water, and the combined organic layers washed successively with dilute hydrocnloric acid, sodium carbonate solution, brine, and then dried over magnesium sulphate. Removal of drying agent and solvents gave a gum which was triturated with 10% ethyl acetate in pentane to give a solid which recrystallised from ethyl acetate—60°-80° petrol to give the title compound as a colourless solid (1.7 g) having m.pt. 156°-7° C.

Anal Found: C,70.22; H,7.01; N,6.77; C23H26N2O4. Requires: C,70.03; H,6.64; N,7.10.

Description 2 t-Butyl-4-(6-cyano-2,2-dimetnyl-trans-3-hydroxy-4-chromanyl)-3-oxo-butyrate

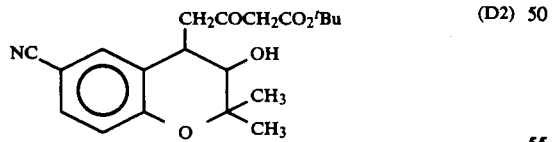
(D2)

The title compound was prepared by the reaction of the dilithium anion of t-butyl acetoacetate with 6-cyano-3,4-dihydro-2,2-dimetnyl-3,4-epoxy-2H-benzo[b]pyran using the method of G. R. Kieczykowski, M. L. Quesada and R. H. Scnlessinger, J. Amer. Chem. Soc., 782, 102, 1980. Chromatography and recrystallisation from ethyl acetate-pentane gave the title compound of m.p. 121.5°-122.5° C.

NMR (CDCl3+D2O) δ 1.21: (3H,s), 1.49 : (12H,s), 3.00-3.65: (4H,m) overlapping, 3.50: (2H,s), 6.88: (1H,d, J=9 Hz), 7.30-7.50: (2H,m),

EXAMPLE 1

Trans-6-cyano-3,4-dihydro-2,2-dimethyl-4-[N,N-dimethyl-2-acetamido]-2H-1-benzopyran-3-ol

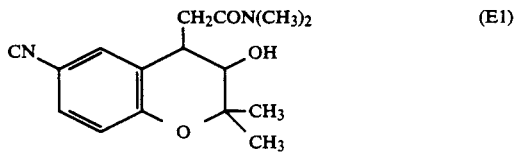
(E1)

n-Butyllithium (6.7 ml of 1.5M solution in hexane, 10 mmol) was added dropwise to a solution of diisopropylamine (1.4 ml, 10 mmol) in tetrahydrofuran (10 ml) at 0° C., under nitrogen. A solution of N,N-dimethylacetamide (0.95 ml, 10mmol) in tetrahydrofuran (10 ml) was then added and the solution stirred for 0.5 hour. A solution of 6-cyano-3,4-epoxy-3,4-dihydro-2,2-dimethyl-2H-1-benzopyran (2.0 g, 10 mmol) in tetrahydrofuran (20 ml) was then added, and the mixture heated under reflux for 2 hours. After cooling, the mixture was partitioned between ethyl acetate and water, and the combined organic layers washed successively with dilute hydrochloric acid, sodium carbonate solution, brine, and then dried over magnesium sulphate. Removal of drying agent and solvents gave a gum which was triturated with pentane and ethyl acetate to give a solid which recrystallised from ethyl acetate/60°-80° petrol to give the required product as colourless plates (0.7 g) having m.pt. 174°-175° C.;

¹H n.m.r. (CDCl3): 1.20: (s, 3H), 1.50: (s, 3H), 2.70-3.70: (m, 4H), 3.05: (s, 3H), 3.10: (s, 3H), 5.20: (m, 1H), 6.85: (d, J=8 Hz, 1H), 7.40: (m, 2H).

EXAMPLE 2

Trans-6-cyano-3,4-dihydro-2,2-dimethyl-4-[N-methyl-2-oxo-3-pyrrolidinyl]-2H-1-benzopyran-3-ol

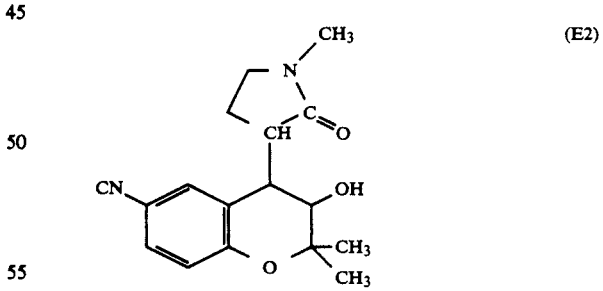
(E2)

A similar procedure to Example 1, replacing N,N-dimethylacetamide with N-methylpyrrolidinone, gave the title compound, which recrystallised from ethyl acetate —60°-80° C. petrol having m.pt. 236°-7° C.;

N.m.r (CDCl3): 1.10: (s, 3H), 1.40: (m, 1H), 1.55: (s, 3H), 1.75: (s, OH), 2.10: (m, 1H), 3.00: (s, 3H), 3 10-3.60: (m, 5H), 6.90: (d, J=10, 1H), 7.25: (d, J=2, 1H), 7.45: (dd, J=10,2, 1H).

Anal. Found: C,68.03; H,6.88; N,9.43; C17H20N2O3. Requires: C,67.98; H,6.71; N,9.33.

EXAMPLE 3

3,4-Dihydro-2,2-dimethyl-3-hydroxy-4-[2-oxo-2-(1-piperidinyl)ethyl]-2H-1-benzopyran-6-carbonitrile

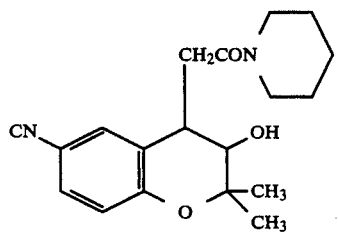
(E3)

A similar procedure to Example 1, replacing N,N-dimethylacetamide with N-acetylpiperidine furnished the title compound, whicn recrystallised from ethyl acetate —60°-80° C. petrol, having m.pt. 160°-1° C.

N.m.r. (CDCl$_3$): 1.20: (s, 3H), 1.50: (s, 3H), 1.55-1.72: (m, 6H), 2.70: (dd, J=17,9, 1H), 3.05: (dd, J=17,3, 1H), 3.35: (dt, J=9,9,3, 1H), 3.47: (t, J=6, 2H), 3.55: (dd, J=9,3, 1H), 3.64: (m, 2H), 5.40: (d, J=3, OH), 6.87: (d, J=9, 1H), 7.40: (dd, J=9,3, 1H), 7.50: (d, J=3, 1H).

Anal. Found: C,69.37; H,7.29; N,8.34; C$_{19}$H$_{24}$N$_2$O$_3$. Requires: C,69.49; H,7.37; N,8.53.

EXAMPLE 4

6-Cyano-3,4-dihydro-3-hydroxy-N-methyl-2,2-dimethyl-2H-1-benzopyran-4-acetamide

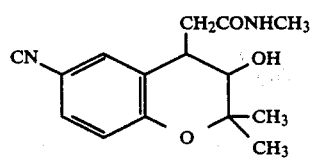
(E4)

A solution of 6-cyano-3,4-dihydro-3-hydroxy-N-methyl-N-(4-methoxy-benzyl)-2,2-dimethyl-2H-1-benzopyran-4-acetamide (0.5 g) in methanesulpnonic acid (5 ml) was stirred at room temperature for 6 days. Water was added, and the mixture extracted into ethyl acetate. The combined organic layers were washed with sodium bicarbonate solution, brine, then dried (MgSO$_4$), filtered and evaporated. Tne crude product was chromatographed (Si gel, ethyl acetate - pentane gradient elution) to give the title compound, which recrystallised from ethyl acetate as a colourless solid (40 mg) having m.pt. 141°-2° C.

N.m.r (CDCl$_3$): 1.20: (s, 3H), 1.50: (s, 3H), 2.65: (dd, J=16,8, 1H), 2.85: (s, 3H), 2.90: (dd, J=16,3, 1H), 3.10: (dt, J=8,8,3, 1H), 3.60: (dd, J=8,3, 1H), 5.30: (d, J=3, OH), 6.85: (d, J=9, 1H), 7.40: (dd, J=9,3, 1H), 7.55: (d, J=3, 1H).

Anal. Found: C,66.07; H,6.92; N,9.87; C$_{15}$H$_{18}$N$_2$O$_3$. Requires C,65.68; H,6.61; N, 10.21.

EXAMPLE 5

Trans-6-cyano-3,4-dihydro-2,2-dimethyl-4-acetonyl-2H-benzo[b]pyran-3-ol

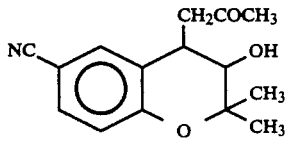
(E5)

To a solution of t-butyl-4-(6-cyano-2,2-dimethyl trans-3-hydroxy-4-chromanyl)-3-oxo butyrate (1 g) in ethanol (50 mls) was added sodium hydroxide (0.28 g) dissolved in water (10 mls). The reaction was heated under reflux for 12 hours, cooled, and water (50 mls) added. After evaporation of the ethanol, the residue was acidified with dilute hydrochloric acid and extracted with ethyl acetate. The organic layer was washed with water and brine, dried over magnesium sulphate, filtered and evaporated to give a gum (0.8 g). Chromatography (chromatotron, pentane-ethyl acetate gradient elution, 2mm silica gel) gave a fraction (450 mgs) whicn was recrystallised from ethyl acetate-pentane to give the title compound (250 mgs) as crystals of m.p. 114°-115° C.

NMR (CDCl$_3$) δ 1.20: (3H, s), 1.49: (3H, s), 2.32: (3H, s), 2.80-3.65: (5H, m), 6.86: (1H, d, J=10 Hz), 7.30-7.50: (2H, m).

EXAMPLE 6

Trans-6-acetamido-3,4-dihydro-2,2-dimethyl-4-acetonyl-2H-1-benzopyran-3-ol

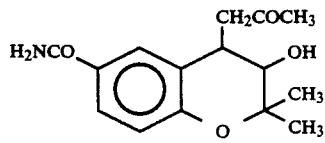
(E6)

In a similar experiment to Example 5, using 2.4 g of t-butyl-4-(6-cyano-2,2-dimethyl-trans-3-hydroxy-4-chromanyl)-3-oxobutyrate, examination of a later fraction from the cnromatotron showed this to contain the title compound (0.38 g) which recrystallised from ethyl acetate-pentane having m.pt. 162°-4° C.

N.m.r. (CDCl$_3$+CD$_3$OD): 1.20: (s, 3H), 1.50: (s, 3H), 2.30: (s, 3H), 3.05: (m, 2H), 3.25-3.60: (m, 2H), 3.40: (s, 3H, NH$_2$, OH), 6.85: (d, 1H), 7.60: (m, 2H).

Pharmacological Data

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12-18 weeks) with systolic blood pressures >170 mmHg were considered hypertensive.

| Compound of Example 1 | Time Post Dose Hours | % Change in Systolic Blood Pressure |
| --- | --- | --- |

15
-continued

| 6 rats | | |
|---|---|---|
| Dose 1 mg/kg | 1 | −45 ± 3 |
| p.o. | 2 | −13 ± 2 |
| Initial Blood | 4 | −28 ± 4 |
| Pressure | | |
| 226 ± 9 mmHg | 6 | −17 ± 2 |

| Compound of Example 5 | Time Post Dose Hours | % Change in Systolic Blood Pressure | % Change in Heart Rate |
|---|---|---|---|
| 6 rats | | | |
| Dose 10 mg/kg | 1 | −30 ± 6 | −3 ± 3 |
| p.o. | 2 | −16 ± 2 | −15 ± 2 |
| Initial Blood | 4 | −13 ± 2 | −7 ± 2 |
| Pressure | | | |
| 264 ± 5 mmHg | 6 | −20 ± 3 | −12 ± 4 |
| Initial Heart | 24 | −1 ± 1 | −7 ± 3 |
| Rate | | | |
| 523 ± 8 beats/ | | | |
| min. | | | |

The compounds of Examples 2,3,4 and 6 were also tested and found to be active in the above test.

I claim:

1. A compound of the formula (I):

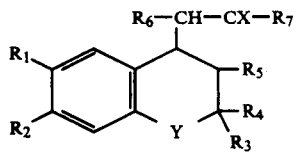

or a pharmaceutically acceptable salt thereof, wherein X is oxygen or sulphur, Y is oxygen, one of $R_1$ and $R_2$ is hydrogen and the other is selected from the group consisting of alkylcarbonyloxy of 1 to 6 carbon atoms in the alkyl moiety, nitro, cyano, chloro, trifluoromethyl, alkylsulphinyl of 1 to 6 carbon atoms in the alkyl moiety, alkylsulphonyl of 1 to 6 carbon atoms in the alkyl moiety, alkoxysulphinyl of 1 to 6 carbon atoms in the alkoxy moiety, alkoxysulphonyl of 1 to 6 carbon atoms in the alkoxy moiety, alkylcarbonylamino of 1 to 6 carbon atoms in the alkyl moiety, alkoxycarbonylamino of 1 to 6 carbon atoms in the alkoxy moiety, alkylthiocarbonyl of 1 to 6 carbon atoms in the alkyl moiety, alkoxythiocarbonyl of 1 to 6 carbon atoms in the alkoxy moiety, alkylthiocarbonyloxy of 1 to 6 carbon atoms in the alkyl moiety, 1-mercaptoalkyl of 2 to 7 carbon atoms in the alkyl moiety, formyl, aminosulphinyl, aminosulphonyl and aminocarbonyl, wherein the amino moiety is unsubstituted or substituted by one or two alkyl moieties of 1 to 6 carbon atoms, or the other of R1 and R2 is alkylsulphinylamino of 1 to 6 carbon atoms in the alkyl moiety, alkylsulphonylamino of 1 to 6 carbon atoms in the alkyl moiety, alkoxysulphinylamino of 1 to 6 carbon atoms in the alkoxy moiety, alkoxysulphonylamino of 1 to 6 carbon atoms in the alkoxy moiety or ethenyl terminally substituted by alkylcarbonyl of 1 to 6 carbon atoms in the alkyl moiety, nitro or cyano; or one of $R_1$ and $R_2$ is nitro, cyano or alkylcarbonyl of 1 to 3 carbon atoms and the other is methoxy or amino unsubstituted or substituted by alkanoyl or 2 to 7 carbon atoms in the alkyl moiety; one of $R_3$ and $R_4$ is hydrogen or alkyl of 1 to 4 carbon atoms and the other is alkyl of 1 to 4 carbon atoms, or $R_3$ and $R_4$ together are polymethylene of 2 to 5 carbon atoms; $R_5$ is hydroxy, alkoxy of of 1 to 6 carbon atoms or unsubstituted aliphatic acyloxy; $R_6$ is hydrogen or alkyl of of 1 to 6 carbon atoms; $R_7$ is $NR_8R_9$ wherein $R_8$ and $R_9$ are each alkyl of of 1 to 6 carbon atoms; or $R_8$ is hydrogen and $R_9$ is alkyl of 1 to 6 carbon atoms; or $R_8$ and $R_9$ together are polymethylene of 4 or 5 carbon atoms; or $R_6$ and $R_8$ together are —$(CH_2)_n$— wherein n is 2 or 3, and $R_9$ is hydrogen or alkyl of of I to 6 carbon atoms; or $R_7$ is $CH_2R_{10}$ wherein $R_{10}$ is hydrogen or alkyl of 1 to 5 carbon atoms; or $R_6$ and $R_{10}$ are —$(CH_2)_m$— wherin m is 2 or 3, the $R_6$—CH—CX—$R_7$ moiety being trans to the $R_5$ moiety.

2. A compound according to claim 1 of the formula (II):

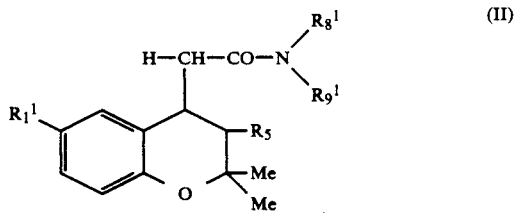

wherein $R_1{}^1$ is nitro, cyano, $CF_3$ or alkylcarbonyl of 1 to 6 carbon atoms in the alkyl moiety; $R_8{}^1$ and $R_9{}^1$ are each alkyl of 1 to 6 carbon atoms; and $R_5$ is hydroxy, alkoxy of 1 to 6 carbon atoms or unsubstituted aliphatic acyloxy.

3. A compound according to claim 1 of the formula (IV):

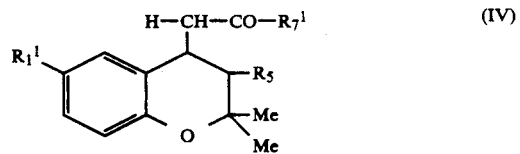

wherein $R_7{}^1$ is alkyl of 1 to 6 carbon atoms, $R_1{}^1$ is nitro, cyano, $CF_3$ or alkylcarbonyl of 1 to 6 carbon atoms in the alkyl moiety and $R_5$ is hydroxy.

4. A pharmaceutical composition useful for treating hypertension in mammals including humans which comprises an antihypertensively effective amount of a compound of the formula (I):

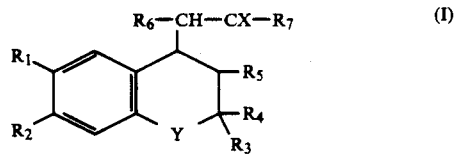

or a pharmaceutically acceptable salt thereof, wherein X is oxygen or sulphur, Y is oxygen, one of $R_1$ and $R_2$ is hydrogen and the other is selected from the group consisting of alkylcarbonyloxy of 1 to 6 carbon atoms in the alkyl moiety, nitro, cyano, chloro, trifluoromethyl, alkylsulphinyl of 1 to 6 carbon atoms in the alkyl moiety, alkylsulphonyl of 1 to 6 carbon atoms in the alkyl moiety, alkoxysulphinyl of 1 to 6 carbon atoms in the alkoxy moiety, alkoxysulphonyl of 1 to 6 carbon atoms in the alkoxy moiety, alkylcarbonylamino of 1 to 6 carbon atoms in the alkyl moiety, alkoxycarbonylamino of 1 to 6 carbon atoms in the alkoxy moiety, alkylthiocarbonyl of 1 to 6 carbon atoms in the alkyl moiety, alkoxythiocarbonyl of 1 to 6 carbon atoms in the alkoxy moiety, alkylthiocarbonyloxy of 1 to 6 carbon atoms in the alkyl moiety, 1-mercaptoalkyl of 2 to 7 carbon atoms in the alkyl moiety, formyl, aminosulphinyl, aminosulphonyl aminocarbonyl, wherein the amino moiety is unsubstituted or substituted by one or two alkyl moieties of 1 to 6 carbon atoms, or the other of $R_1$ and $R_2$ is alkylsuphinylamino of 1 to 6 carbon atoms in the alkyl moiety, alkylsulphonylamino of 1 to 6 carbon atoms in the alkyl moiety, alkoxysulphinylamino of 1 to 6 carbon atoms in the alkoxy moiety, alkoxysulphonylamino of 1 to 6 carbon atoms in the alkoxy moiety or ethenyl terminally substituted by alkylcarbonyl of 1 to 6 carbon atoms in the alkyl moiety, nitro or cyano; or one of $R_1$ and $R_2$ is nitro, cyano or alkylcarbonyl of 1 to 3 carbon atoms and the other is methoxy or amino unsubstituted or substituted by alkanoyl or 2 to 7 carbon atoms in the alkyl moiety; one of $R_3$ and $R_4$ is hydrogen or alkyl of 1 to 4 carbon atoms and the other is alkyl of 1 to 4 carbon atoms, or $R_3$ and $R_4$ together are polymethylene of 2 to 5 carbon atoms; $R_5$ is hydroxy, alkoxy of 1 to 6 carbon atoms or unsubstituted aliphatic acyloxy; $R_6$ is hydrogen or alkyl of 1 to 6 carbon atoms; $R_7$ is $NR_8R_9$ wherein $R_8$ and $R_9$ are each alkyl of 1 to 6 carbon atoms; or $R_8$ is hydrogen and $R_9$ is alkyl of 1 to 6 carbon atoms; or $R_8$ and $R_9$ together are polymethylene of 4 or 5 carbon atoms; or $R_6$ and $R_8$ together are —$(CH_2)_n$— wherein n is 2 or 3, and $R_9$ is hydrogen or alkyl of 1 to 6 carbon atoms; or $R_7$ is $CH_2R_{10}$ wherein $R_{10}$ is hydrogen or alkyl of 1 to 5 carbon atoms; or $R_6$ and $R_{10}$ are —$(CH_2)_m$— wherein m is 2 or 3, the $R_6$—CH—CX—$R_7$ moiety being trans to the $R_5$ moiety, in combination with a pharmaceutically acceptable carrier.

5. A composition according to claim 4 wherein the compound is of the formula (II):

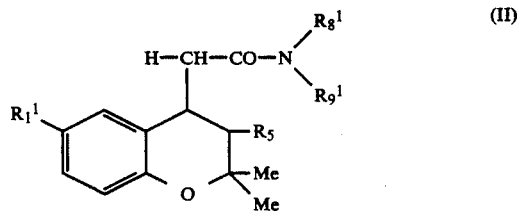

wherein $R_1^1$ is nitro, cyano, $CF_3$ or alkylcarbonyl of 1 to 6 carbon atoms in the alkyl moiety; $R_8^1$ and $R_9^1$ are each alkyl of 1 to 6 carbon atoms; and $R_5$ is hydroxy, alkoxy of 1 to 6 carbon atoms or unsubstituted aliphatic acyloxy.

6. A composition according to claim 4 wherein the compound is of the formula (IV):

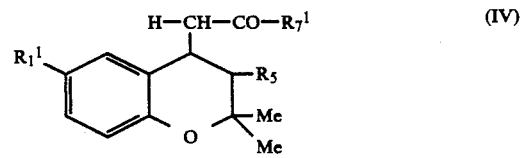

wherein $R_7^1$ is alkyl of 1 to 6 carbon atoms, $R_1^1$ is nitro, cyano, $CF_3$ or alkylcarbonyl of 1 to 6 carbon atoms in the alkyl moiety and $R_5$ is hydroxy.

7. A composition according to claim 4 wherein the compound is trans-6-cyano-3,4-dihydro-2,2-dimethyl-4-[N,N-dimethyl-2-acetamido]-2H-1-benzopyran-3-ol.

8. A method of treating hypertension in mammals including humans which comprises administering to such a mammal in need thereof in antihypertensively amount of a compound of the formula (I):

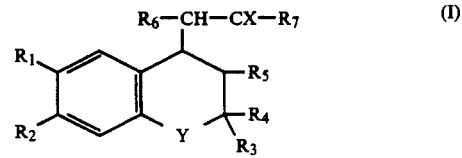

or a pharmaceutically acceptable salt thereof, wherein X is oxygen or sulphur, Y is oxygen, one of $R_1$ and $R_2$ is hydrogen and the other is selected from the group consisting of alkylcarbonyloxy of 1 to 6 carbon atoms in the alkyl moiety, nitro, cyano, chloro, trifluoromethyl, alkylsulphinyl of 1 to 6 carbon atoms in the alkyl moiety, alkylsulphonyl of 1 to 6 carbon atoms in the alkyl moiety, alkoxysulphinyl of 1 to 6 carbon atoms in the alkoxy moiety, alkoxysulphonyl of 1 to 6 carbon atoms in the alkoxy moiety, alkylcarbonylamino of 1 to 6 carbon atoms in the alkyl moiety, alkoxycarbonylamino of 1 to 6 carbon atoms in the alkoxy moiety, alkylthiocarbonyl of 1 to 6 carbon atoms in the alkyl moiety, alkoxythiocarbonyl of 1 to 6 carbon atoms in the alkoxy moiety, alkylthiocarbonyloxy of 1 to 6 carbon atoms in the alkyl moiety, 1-mercaptoalkyl of 2 to 7 carbon atoms in the alkyl moiety, formyl, aminosulphinyl, aminosulphonyl and aminocarbonyl, wherein the amino moiety is unsubstituted or substituted by one or two alkyl moieties of 1 to 6 carbon atoms, or the other of $R_1$ and $R_2$ is alkylsulphinylamino of 1 to 6 carbon atoms in the alkyl moiety, alkylsulphonylamino of 1 to 6 carbon atoms in the alkyl moiety, alkoxysulphinylamino of 1 to 6 carbon atoms in the alkoxy moiety, alkoxysulphonylamino of 1 to 6 carbon atoms in the alkoxy moiety or ethenyl terminally substituted by alkylcarbonyl of 1 to 6 carbon atoms in the alkyl moiety, nitro or cyano; or one of $R_1$ and $R_2$ is nitro, cyano or alkylcarbonyl of 1 to 3 carbon atoms and the other is methoxy or amino unsubstituted or substituted by alkanoyl or 2 to 7 carbon atoms in the alkyl moiety; one of $R_3$ and $R_4$ is hydrogen or alkyl of 1 to 4 carbon atoms and the other is alkyl of 1 to 4 carbon atoms, or $R_3$ and $R_4$ together are polymethylene of 2 to 5 carbon atoms; $R_5$ is hydroxy, alkoxy of 1 to 6 carbon atoms or unsubstituted aliphatic acyloxy; $R_6$ is hydrogen or alkyl of 1 to 6 carbon atoms; $R_7$ is $NR_8R_9$ wherein $R_8$ and $R_9$ are each alkyl of 1 to 6 carbon atoms; or $R_8$ is hydrogen and $R_9$ is alkyl of 1 to 6 carbon atoms; or $R_8$ and $R_9$ together are polymethylene of 4 or 5 carbon atoms; or $R_6$ and $R_8$ together are —$(CH_2)_n$— wherein n is 2 or 3, and $R_9$ is hydrogen or alkyl of 1 to 6 carbon atoms; or $R_7$ is $CH_2R_{10}$ wherein $R_{10}$ is hydrogen or alkyl of 1 to 5 carbon atoms; or $R_6$ and $R_{10}$ are —$(CH_2)_m$— wherein m is 2 or 3, the $R_6$—CH—CX—$R_7$ moiety being trans to the $R_5$ moiety, in combination with a pharmaceutically acceptable carrier.

9. A method according to claim 8 wherein the compound is of the formula (II):

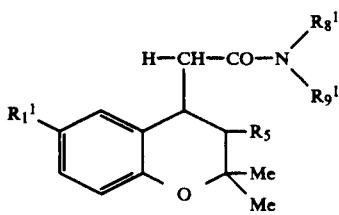

(II)

wherein $R_1^1$ is nitro, cyano, $CF_3$ or alkylcarbonyl of 1 to 6 carbon atoms in the alkyl moiety; $R_8^1$ and $R_9^1$ are each alkyl of 1 to 6 carbon atoms; and $R_5$ is hydroxy, alkoxy of 1 to 6 carbon atoms or unsubstituted aliphatic acyloxy.

10. A method according to claim 8 wherein the compound is of the formula (IV):

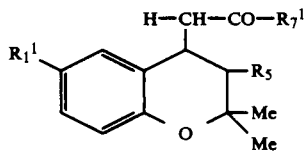

(IV)

wherein $R_7^1$ is alkyl of 1 to 6 carbon atoms, $R_1^1$ is nitro, cyano, $CF_3$ or alkylcarbonyl of 1 to 6 carbon atoms in the alkyl moiety and $R_5$ is hydroxy.

11. A method according to claim 8 wherein the compound is trans-6-cyano-3,4-dihydro-2,2-dimethyl-4-[N,N-dimethyl-2-acetamido]-2H-1-benzopyran-3-ol.

12. A compound selected from the group consisting of trans-6-cyano-3,4-dihydro-2,2-dimethyl-4-[N,N-dimethyl-2-acetamido]-2H-1-benzopyran-3-ol,
3,4-dihydro-2,-dimethyl-3-hydroxy-4-[2-oxo-2-(1-piperidinyl)ethyl]-2H-1-benzopyran-6-carbonitrile,
6-cyano-3,4-dihydro-3-hydroxy-N-methyl-2,2-dimethyl-2H-1-benzopyran-4-acetamide,
trans-6-cyano-3,4-dihydro-2,2-dimethyl-4-acetonyl-2H-benzopyran-3-ol and trans-6-aminocarbonyl-3,4-dihydro-2,2-dimethyl-4-acetonyl-2H-1-benzopyran-3-ol.

13. A composition according to claim 4 wherein the compound is selected from the group consisting of trans-6-cyano-3,4-dihydro-2,2-dimethyl-4-[N,N-dimethyl-2-acetamido]-2H-1-benzopyran-3-ol,
3,4-dihydro-2,-dimethyl-3-hydroxy-4-[2-oxo-2-(1-piperidinyl)ethyl]-2H-1-benzopyran-6-carbonitrile,
6-cyano-3,4-dihydro-3-hydroxy-N-methyl-2,2-dimethyl-2H-1-benzopyran-4-acetamide,
trans-6-cyano-3,4-dihydro-2,2-dimethyl-4-acetonyl-2H-benzopyran-3-ol and
trans-6-aminocarbonyl-3,4-dihydro-2,2-dimethyl-4-acetonyl-2H-1-benzopyran-3-ol.

14. A method according to claim 8 wherein the compound is selected from the group consisting of trans-6-cyano-3,4-dihydro2,2-dimethyl-4-[N,N-dimethyl-2-acetamido]-2H-1-benzopyran-3-ol,
3,4-dihydro-2,-dimethyl-3-hydroxy-4-[2-oxo-2-(1-piperidinyl)ethyl]-2H-1-benzopyran-6-carbonitrile,
6-cyano-3,4-dihydro-3-hydroxy-N-methyl-2,2-dimethyl-2H-1-benzopyran-4-acetamide,
trans-6-cyano-3,4-dihydro-2,2-dimethyl-4-acetonyl-2H-benzopyran-3-ol and
trans-6-aminocarbonyl-3,4-dihydro-2,2-dimethyl-4-acetonyl-2H-1-benzopyran-3-ol.

15. The compound 6-cyano-3,4-dihydro-3-hydroxy-N-methyl-N-4-methoxy-benzyl)-2,2-dimethyl-2H-1-benzopyran-4-acetamide.

16. The compound trans-6-cyano-3,4-dihydro-2,2-dimethyl-4-[N,N-dimethyl-2-acetamido]-2H-1-benzopyran-3-ol.

* * * * *